United States Patent [19]

Aaltonen et al.

[11] Patent Number: 4,886,528
[45] Date of Patent: Dec. 12, 1989

[54] TUBULAR WATER SEPARATOR FOR A GAS ANALYZER

[75] Inventors: Olli Aaltonen; Antti Martikainen, both of Vantaa; Börje Rantala, Helsinki; Jan Ekström, Helsinki; Osmo Toikka, Helsinki, all of Finland

[73] Assignee: Instrumentarium Corp., Finland

[21] Appl. No.: 193,335

[22] Filed: May 12, 1988

[30] Foreign Application Priority Data

May 5, 1987 [FI] Finland ................................ 871975

[51] Int. Cl.⁴ ............................................. B01D 13/00
[52] U.S. Cl. ......................................... 55/158; 55/270; 73/863.23; 128/719
[58] Field of Search .................. 55/270, 274, 350, 158; 73/863.23; 128/716, 719

[56] References Cited

U.S. PATENT DOCUMENTS 2,966,235 12/1960 Kammermeyer ........................ 55/16
3,367,850 2/1968 Johnson ................................. 55/16
4,558,708 12/1985 Labuda et al. ...................... 128/719

Primary Examiner—Bernard Nozick
Attorney, Agent, or Firm—Andrus, Sceales, Starke & Sawall

[57] ABSTRACT

The invention relates to a water separator for a gas analyzer, comprising a tube (12) for passing a gas sample into the water separator, wherein water separation is effected in a tubular passage by dividing the flow into two partial flows. The wall or walls (3) of a first tubular passage (17) are made of a porous material, readily permeable to gas, and this main flow, which has penetrated the wall, is passed into a second tubular passage (4) and via a tube (10) on to measuring sensors (5 and 6) but the water, which is not able to penetrate the porous wall of first passage (17), is passed along with a minor amount of gas down a passage (17, 13) into a water receiver (15) and this many times lesser side flow further via a tube (14) into a third tubular passage (16), through its porous wall (3) into a fourth tubular passage (18) and via a tube (11) through a flow throttle (7) on to a pump (8).

9 Claims, 2 Drawing Sheets

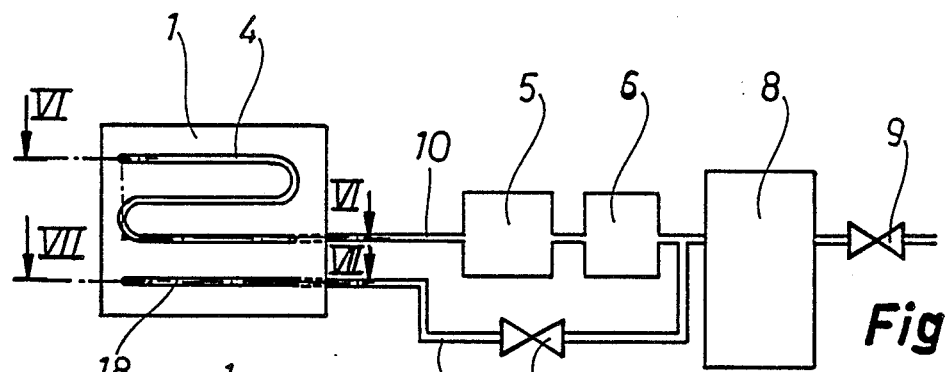
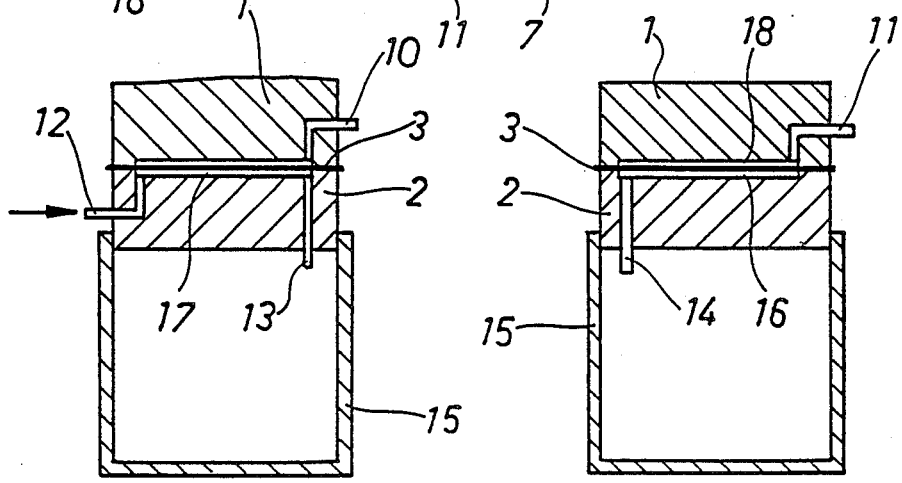
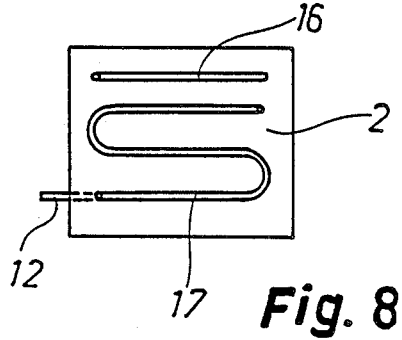

TUBULAR WATER SEPARATOR FOR A GAS ANALYZER

The present invention relates to a tubular water separator for a gas analyzer, comprising a tube for passing a gas sample to a water separator, provided with a porous hose through whose wall the gas sample is sucked by way of a porous hose-surrounding tubular space further to a measuring sensor and the condensation water remaining inside the porous hose is sucked along with a minor amount of gas into a water receiver.

BACKGROUND OF THE INVENTION

For example, when using a $CO_2$ analyzer for measuring alveolar air, a problem encountered is the water vapour contained in exhalation air. Since temperature in a sampling passage is lower than human body temperature, the water vapour condensates in a measuring device and the intrusion of water drops inside a measuring sensor results in the failure of a measurement. In addition, a gas ample often entraps mucus and blood as well as dust which the water separator must also be capable of removing from the gas.

In prior known gas analyzers, water has been removed from a gas sample by using a water separator, provided with a water-separation chamber which divides the flow into two partial flows in a manner that the main flow is sucked through a measuring sensor by means of a tube connected with the water-separation chamber and the many times lesser side flow is sucked continuously by way of a tube connected with the bottom section of said water-separation chamber into a water receiver for retaining therein the water contained in a gas sample and further on to a pump. This prior known solution involves the following drawbacks. The water-separation chamber results in extra volume in the passage of a gas sample, which leads to slower measuring. A drawback is also the failure of a water separation step. Inevitably, some water gets on a measuring sensor e.g. as a result of splshing in the separation chamber or some water finds its way to the pump after a water vessel in the side-flow branch is filled.

Another prior art method is the use of a moisture-equalizing tube. In this case, the analyzer is not usually fitted with an individual water separator but, instead, a sampling tube between a patient and the apparatus as well as a tube between s sampling connector in the apparatus and a mesuring sensor are made of a material which equalizes moisture of the gas inside the tube to be the same as that on the outside, so that water always tends to work its towards the drier side, the moisture of a gas sample equalizing to be the same as the moisture of ambient air and no condensation occurs on the tube walls.

This prior art solution involves the following drawbacks. The tube material is only capable of a limited transfer of water through the wall per unit time, whereby the water splashed from the tubing of a respiration apparatus, a patient's mucus or blood may end up on a measuring sensor. Dust in the air also finds its way to a measuring sensor and causes problems there.

SUMMARY OF THE INVENTION

An object of the invention is to provide a water separator capable of resolving the above problems. A particular object of the invention has been to prevent the entrance of all liquids and dust under any circumstances inside an analyzer, especially onto measuring sensors, while maintaining the high speed of measuring.

In order to accomplish the object and objectives of the invention, a water separator of the invention for a gas analyzer is characterized in that the wall or walls of a first tubular passage are made of a porous material highly permeable to gas and this main flow penetrated through the wall is passed into a second tubular passage and through the tube on to measuring sensors but the water, which is not admitted through the porous wall of said first passage, is passed along with a minor amount of gas down the passage into a water receiver and this many times lesser side flow onwards through the tube into a third tubular passage through whose porous wall the side flow is passed into a fourth tubular passage and by way of the tube through a flow restrictor on to a pump. Thus, a gas sample travels in a tubular space in the water separator and is sucked through a porous wall into a tubular space and further on to a measuring sensor, whereby the water does not pass through a porous wall at a negative pressure caused by a gas sample pump but, instead, is passed, so separated from a gas sample, into a water receiver with or without a minor side flow.

In a most preferred embodiment of the invention, the main flow is adapted to fork into two partial flows in a manner that the main flow is sucked through a porous wall and passed on to a measuring sensor, the side flow is passed by way of a water receiver through a porous wall on to a sample pump in order to prevent the passage of water inside the apparatus even when the water receiver is filled, since the porous wall prevents the passage of water therethrough by the action of negative pressure generated by the gas sample pump. Thus, the condensation water, mucus, dust and water remain in the water separator of such apparatus and are collected in water receiver and under no circumstances are allowed inside the apparatus with the result that neither bacteria nor viruses contained in the liquids are able to work their into the apparatus. The restrictors or throttles fitted upstream and downstream of a sample pump can be used to regulate the mutual relationship between main and side flows. In order to prevent a side flow from substantially affecting the speed of measuring, it must be considerably lesser than the main flow, preferably circa 5% of the entire sample flow.

As for the manufacturing technique, such tubular components can be obtained by forming them on the boundary surface of two elements fastened gas-tightly to each other in a manner that each element is provided with a cross-sectionally semi-circular groove and between the elements is fitted a porous membrane or the groove is fitted with a porous tube. One of these elements can be fitted with a removable water receiver and a membrane component for the side flow or, alternatively, the side flow can be passed through a membrane fitted between the elements.

DESCRIPTION OF THE DRAWINGS

The invention will now be described in more detail with reference made to the accompanying drawings, in which

FIG. 5 is a view similar to FIG. 1 showing a second embodiment of a water separator of the invention for a gas analyzer.

FIG. 6 is a sectional view along lines VI—VI in FIG. 5;

FIG. 7 is a sectional view along lines VII—VII in FIG. 5.

FIG. 8 shows a boundary surface of element 2 seen in FIGS. 6 and 7.

DESCRIPTION OF THE ILLUSTRATED EMBODIMENT

Figure 1:
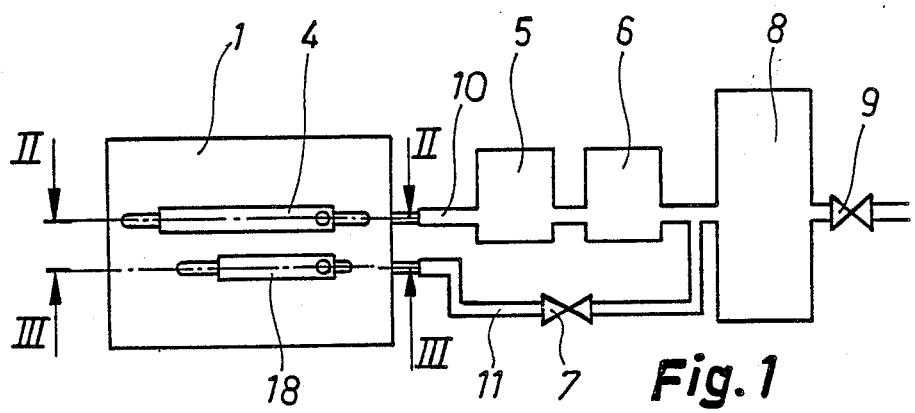
FIG. 1 shows a water separator according to one embodiment of the invention connected with a gas analyzer, which is shown schematically.

A gas sample is brought from a patient along a plastic tubing via a tube 12 into a passage 17 whose cross-sectional shape is semi-circular or circular. In passage 17 a gas sample divides into two partial flows. The main flow is sucked by means of a pump 8 through the porous wall 3 of passage 17 into a passage 4 having semi-circular or circular cross-section and further on via a tube 10 as well as measuring sensors 5 and 6. Circa 5% of the sample flow is sucked by means of pump 8 by way of a tube 13 into a water receiver 15 and further by way of a tube 14 into a passage 16 having semi-circular or circular cross-section and through the porous wall 3 of tubular passage 16 into a passage 18 having semi-circular or circular cross-section and further on via a tube 11 and a flow throttle 7 to combine it with the main flow. A flow throttle 9 mounted downstream of pump 8 is used to adjust the overall flow as proper.

Figure 2:
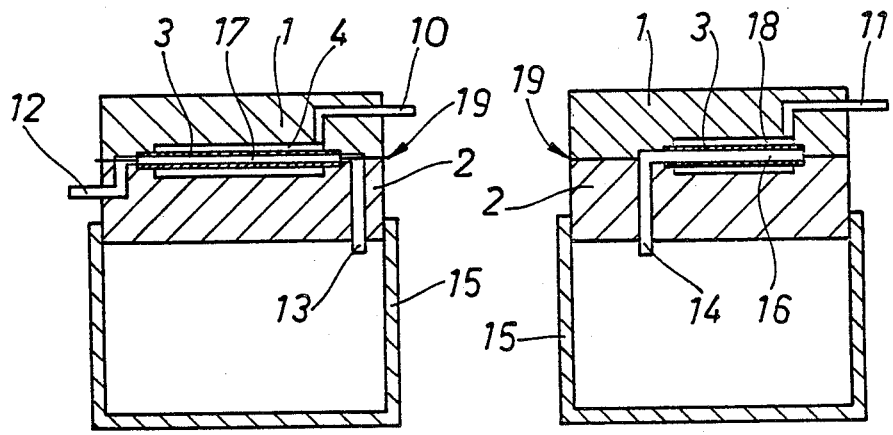
FIG. 2 is a sectional view along the lines II—II in FIG. 1.
Figure 3:
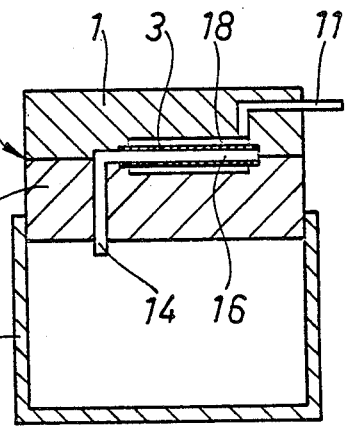
FIG. 3 is a sectional view along the lines III—III in FIG. 1.
Figure 4:
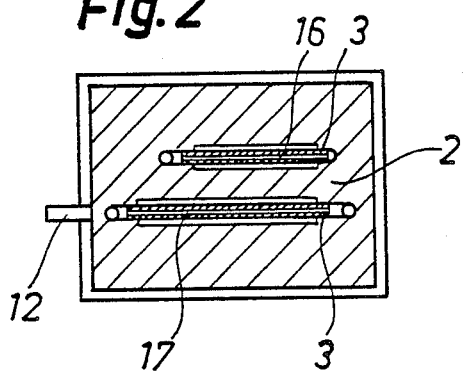
FIG. 4 shows a sectional view at a boundary surface 19 between elements 1 and 2 in FIGS. 2 and 3.

In the embodiment shown in FIGS. 1 to 4, the boundary surface of mutually gas-tightly fitted elements 1 and 2 is provided with cross-sectionally circular grooves 4 and 18, fitted with porous tubings 3, 17 and 3, 16.

The outer diameter of such porous tubings is somewhat smaller than the inner diameter of grooves 4 and 18 to provide two concentric tubular passages separated from each other by porous wall 3.

In the embodiment shown in FIGS. 5 to 8, between mutually gas-tightly fitted elements 1 and 2 is mounted a porous membrane or diaphragm in a manner that tubular passages 17 and 4 and respectively 16 and 18 are formed on opposite sides of diaphragm 3. The length of passages 17 and 4 has been increased by making the passages winding.

The porous, water-impermeable diaphragm 3 must be squeezed tightly between elements 1 and 2 for preventing the mixing of a gas sample, which would slow down the measuring. Diaphragm 3 must be fitted in a gas-tight manner between elements 1 and 2, so that the gas travels along the passage instead of passing transversely from the end of such passage e.g. towards the centre of a passage. Leakage from one passage to another or to ambient air is not allowed, either.

The above-described assembly accomplishes the result that gas travels all the time in a water separator in a condition resembling as closely as possible a conventional tubing, whereby the measurement-impeding mixing of gas is as negligible as possible.

We claim:

1. A water separator for a gas analyzer, comprising a housing, a first chamber disposed within said housing, a second chamber disposed within said housing, a wall formed of a gas permeable and liquid impermeable material separating said chambers, means for introducing a gas sample containing a liquid into said first chamber with a first portion of the gas passing through said wall to the second chamber and a second portion of the gas and said liquid remaining in the first chamber, means for flowing said first portion of the gas from the second chamber to a measuring unit, a receptacle mounted on the housing, a first conduit connecting said first chamber and said receptacle for conducting said second portion of said gas and said liquid to said receptacle, and a second conduit connecting the upper end portion of said receptacle with a source of vaccum for removing said second portion of said gas from said receptacle.

2. The separator of claim 1, wherein said wall is cylindrical in shape and said first chamber is on the inside of said cylindrical wall and said second chamber is annular and is located on the outside of said wall.

3. The separator of claim 1, wherein said wall is a flat diaphragm and said first and second chambers are disposed on opposite sides of said diaphragm.

4. The separator of claim 1, wherein said housing is composed of a pair of sections having contiguous surfaces, said surfaces having mating grooves constituting said second chamber, said wall comprising a tubular member disposed within said mating grooves with the interior of said tubular member constituting said first chamber.

5. The separator of claim 1, wherein said housing is composed of a pair of sections having contiguous surfaces, said surfaces having mating grooves, said wall comprising a diaphragm interposed between said surfaces and extending across said grooves, said first chamber being located on one side of said diaphragm and said second chamber being located on the opposite side of said diaphragm.

6. A water separator for a gas analyzer, comprising a housing, a first chamber disposed within said housing, a second chamber disposed within said housing, a wall formed of a gas permeable and liquid impermeable material separating said chambers, means for introducing a gas sample containing a liquid into said first chamber with a first portion of the gas passing through said wall to the second chamber and a second portion of the gas and said liquid remaining in the first chamber, means for flowing said first portion of the gas from the second chamber to a measuring unit, means defining a third chamber and a fourth chamber, a second wall formed of a gas permeable and liquid impermeable material separating said third and fourth chambers, means for flowing the second portion of said gas and said liquid from said first chamber to said third chamber, the second portion of said gas passing through said second wall to said fourth chamber, and discharge means for discharging the second portion of said gas from said fourth chamber.

7. The separator of claim 6, wherein said discharge means comprises a discharge conduit connected to said fourth chamber, and suction means connected to said discharge conduit for drawing said gas from said fourth chamber through said discharge conduit.

8. The separator of claim 7, and including flow control means disposed in said discharge conduit for controlling the flow of gas through said discharge conduit.

9. A water separator for a gas analyzer, comprising a housing, a first chamber disposed within said housing, a second chamber disposed within said housing, a wall formed of a gas permeable and liquid impermeable material separating said chambers, means for introducing a gas sample containing a liquid into said first chamber with a first portion of the gas passing through said wall to the second chamber and a second portion of the gas and said liquid remaining in the first chamber, means for flowing said first portion of the gas from the second chamber to a measuring unit, water receiving means connected to said first chamber for receiving the second portion of said gas and for separating liquid from the second portion of said gas, a third chamber connected to said water receiving means, a fourth chamber, a second wall formed of a gas permeable and liquid impermeable material separating said third and fourth chambers, means for flowing the second portion of said gas and any remaining liquid from said water receiving means to said third chamber, said second portion of said gas passing through said second wall to said fourth chamber, and discharge means for discharging said second portion from the fourth chamber.

* * * * *